US009757550B1

(12) United States Patent
    Alam

(10) Patent No.: US 9,757,550 B1
(45) Date of Patent: Sep. 12, 2017

(54) DISPENSING DEVICE

(71) Applicant: KING SAUD UNIVERSITY, Riyadh (SA)

(72) Inventor: Mohd Aftab Alam, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 15/426,003

(22) Filed: Feb. 6, 2017

(51) Int. Cl.
    A61M 31/00    (2006.01)
    B05C 17/01    (2006.01)
    A61M 5/315    (2006.01)

(52) U.S. Cl.
    CPC ....... A61M 31/007 (2013.01); B05C 17/0109 (2013.01); B05C 17/0113 (2013.01); A61M 5/31511 (2013.01); A61M 2005/31518 (2013.01)

(58) Field of Classification Search
    CPC ............ B05C 17/0109; B65D 83/005; A61M 2005/31518; A61M 31/007
    See application file for complete search history.

(56) References Cited

U.S. PATENT DOCUMENTS

| | | | | |
|---|---|---|---|---|
| 876,968 A * | 1/1908 | James | ............... | B67D 1/103 184/38.2 |
| 1,021,451 A * | 3/1912 | Craven | ............... | B05C 17/0109 222/390 |
| 1,025,511 A * | 5/1912 | Craven | ............... | B05C 17/0109 222/392 |
| 1,036,970 A * | 8/1912 | Craven | ............... | B05C 17/0109 222/392 |
| 1,765,794 A * | 6/1930 | Hirth | ............... | B65D 1/06 215/378 |
| 2,012,396 A * | 8/1935 | Luce | ............... | B65D 35/40 222/392 |
| 4,421,504 A * | 12/1983 | Kline | ............... | A61M 31/007 604/12 |
| 4,917,273 A * | 4/1990 | Seager | ............... | A46B 11/0024 222/145.3 |
| 5,484,087 A * | 1/1996 | Negrych | ............... | B65D 83/0011 116/323 |
| 7,306,578 B2 * | 12/2007 | Gray | ............... | A61M 5/1456 604/151 |
| 8,747,346 B2 | 6/2014 | Hochberg | | |
| 2002/0008123 A1 * | 1/2002 | Nakayoshi | ............... | B65D 81/2023 222/386 |

(Continued)

Primary Examiner — Kevin C Sirmons
Assistant Examiner — William Carpenter
(74) Attorney, Agent, or Firm — Richard C. Litman

(57) ABSTRACT

The dispensing device includes a hollow tube having an open upper end and an open lower end, as well as a horizontal bar disposed between the walls of the hollow tube adjacent to the open lower end. A disc is movably positioned within the hollow tube, the disc having a central aperture defined therein. A string or other flexible member has one end secured to the disc. The other end of the string is drawn downward in the tube, looped around the horizontal bar, then drawn upward through the central aperture in the disc and out the open upper end of the tube. A semi-solid medication is loaded in the tube between the disc and the open lower end of the tube. When the string is pulled out of the upper end of the tube, the disc is drawn downward, dispensing the medication.

8 Claims, 4 Drawing Sheets

(56) References Cited

U.S. PATENT DOCUMENTS

2004/0049162 A1* 3/2004 Fisher .................... A61M 5/34
                                                    604/240
2008/0097286 A1* 4/2008 Cleator ................ A61M 31/00
                                                    604/48

* cited by examiner

DISPENSING DEVICE

BACKGROUND OF THE INVENTION

1. Field of the Invention

The present invention relates to dispensers, and particularly to a plunger-free dispensing device for the delivery of semi-solid pharmaceutical preparations into a body cavity, such as the vagina or rectum.

2. Description of the Related Art

Various vaginal and/or rectal conditions are treated locally by applying a pharmaceutical preparation formulated as a gel, cream, or ointment to the vagina or the rectum (both of which are hereinafter referred to as a "body cavity"), as appropriate. Sometimes the pharmaceutical preparation is inserted into the body cavity for its systemic effects. These preparations are normally applied using an applicator, which can successfully deliver the pharmaceutical product into the body cavity.

Vaginal and/or rectal applicators are well known in the art. Such applicators typically include a hollow barrel and a plunger positioned inside the barrel for the delivery of the pharmaceutical preparation. For example, the hollow barrel may be filled with the recommended/prescribed amount of pharmaceutical preparation. Once the hollow barrel is filled with the recommended quantity of preparation, the barrel is inserted into the body cavity and the preparation is delivered into the body cavity by pushing the plunger. Some of these applicators can be re-used after proper washing or cleaning. The washing or cleaning of these applicators after dispensing the preparation can be unpleasant and non-complying. For example, if the re-useable applicator is not cleaned properly, then it may lead to the reinfection or the spread of disease.

Although such body cavity applicators can deliver the pharmaceutical preparation successfully, such applicators may require an unnecessarily long plunger. The plunger not only increases the size of the packaging, but also increases the amount of material required to make the applicator.

Thus, a dispensing device solving the aforementioned problems is desired.

SUMMARY OF THE INVENTION

The dispensing device includes a hollow tube having an open upper end and an open lower end, as well as a horizontal bar disposed between the walls of the hollow tube adjacent to the open lower end. A disc is movably positioned within the hollow tube, the disc having a central aperture defined therein. A string or other flexible member has one end secured to the disc. The other end of the string is drawn downward in the tube, looped around the horizontal bar, then drawn upward through the central aperture in the disc and out the open upper end of the tube. A semi-solid medication is loaded in the tube between the disc and the open lower end of the tube. When the string is pulled out of the upper end of the tube, the disc is drawn downward, dispensing the medication.

The tube may have an external annular flange at the upper end to aid in holding the tube. The tube may have graduated indicia along the length of the tube corresponding to the volume of medication being dispensed. A pull, such as a ring or a ball, may be attached to the free end of the string opposite the end attached to the disc. The pull may have a greater diameter than the internal diameter of the tube to prevent the free end of the string from falling into the tube.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
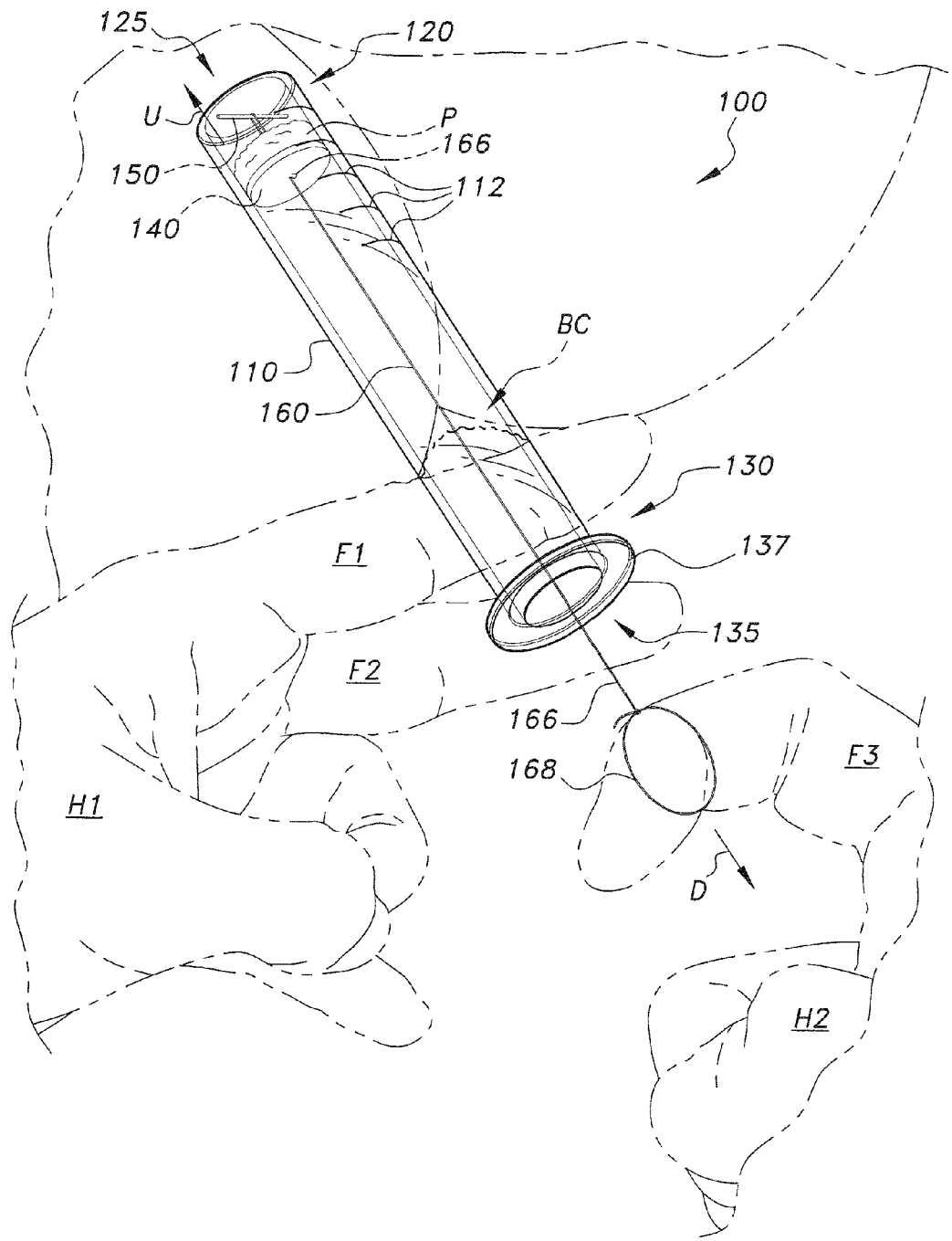
FIG. 1 is an environmental, perspective view of a dispensing device according to the present invention.
Figure 2:
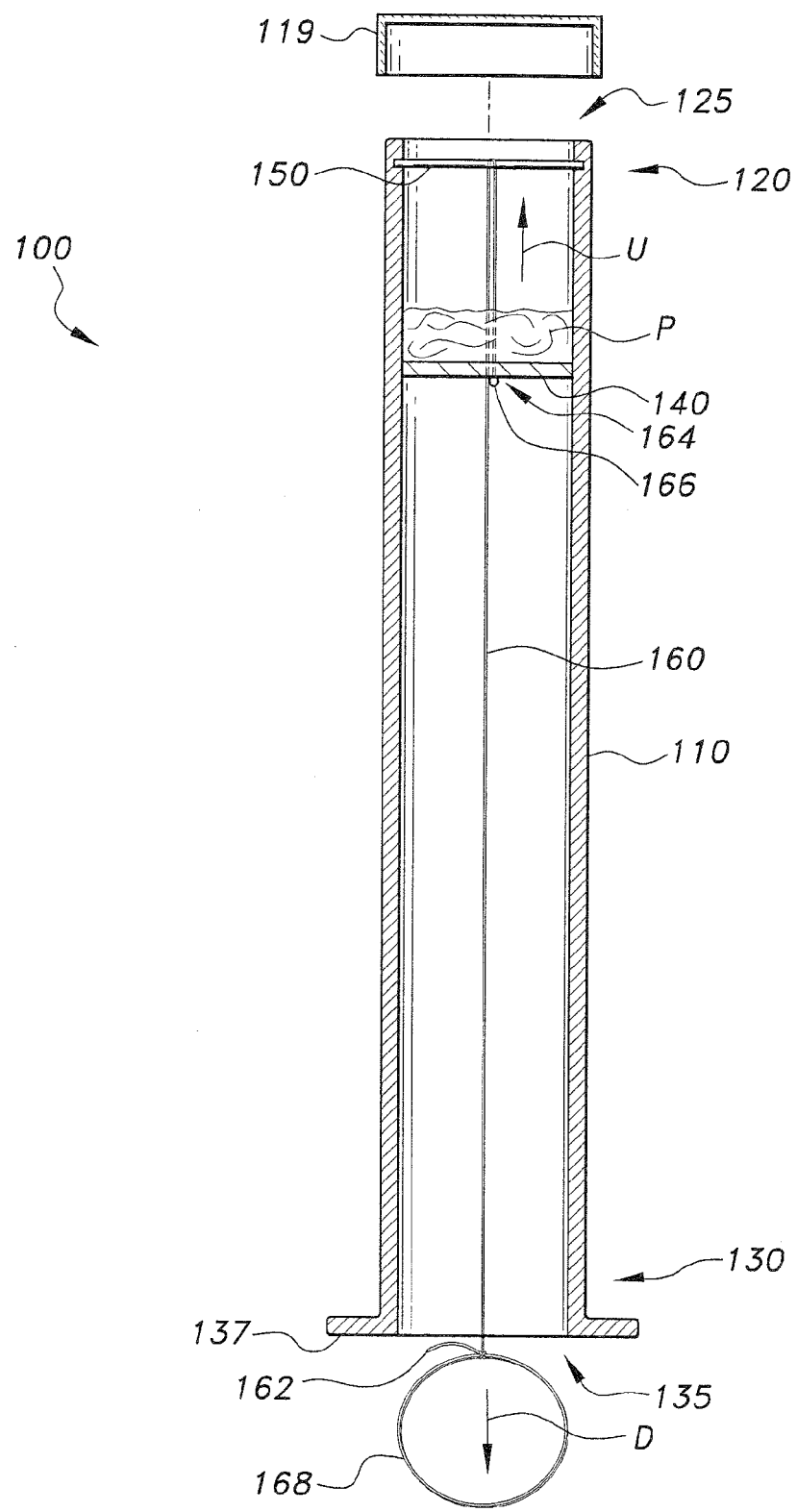
FIG. 2 is an elevation view in section of a dispensing device according to the present invention.

FIGS. 1-4 show a dispensing device 100 for delivering a predetermined amount of a pharmaceutical preparation P, such as a gel, a cream, an ointment, or other semi-solid pharmaceutical preparation, into a body cavity BC, such as the vagina or rectum. The device 100 includes a cylindrical hollow tube 110 having an upper end 130 and a lower end 120. The upper end 130 has an upper opening 135 and the lower end 120 has a lower opening 125 defining a dispensing/refill port. The device 100 also includes a disc 140 movably positioned inside the hollow tube 110. A horizontal bar 150 extends transversely between opposing side walls at the lower end 120 of the hollow tube 110. A string 160 or other flexible filamentous member is attached to the disc 140 and routed through the tube 110 in a manner described below so that when the string 160 is pulled, the disc 140 pushes the pharmaceutical preparation P out of the lower end 120 of the tube 110 and into the body cavity BC.

The cylindrical tube 110 can be formed from any suitable, medical grade transparent material, preferably plastic, and can have any length suitable for dispensing the pharmaceutical preparation P into the body cavity BC and onto the infected area. Further, the tube 110 has a uniform internal diameter. It is to be noted that the diameter of the tube 110 can vary, depending upon the body cavity BC within which the lower end 120 of the hollow tube 110 is to be inserted and the amount of pharmaceutical preparation P required to be dispensed. The lower opening 125 is the dispensing end (i.e., the end through which the pharmaceutical preparation P is dispensed into the body cavity BC and onto the infected area).

The upper end 130 of the device 100 can include an external annular flange 137 extending around the outer periphery of the upper end 130 of the tube 110. The flange 137 is configured for helping a person to hold the device 100, as well as to prevent him or her from inserting the hollow tube 110 too far into the body cavity BC. It is to be noted that the outer surface of the tube 110 can include uniquely identifiable indicia, such as graduation marks 112, to aid in measuring the predetermined volume of pharmaceutical preparation P within the device 100.

Figure 3:
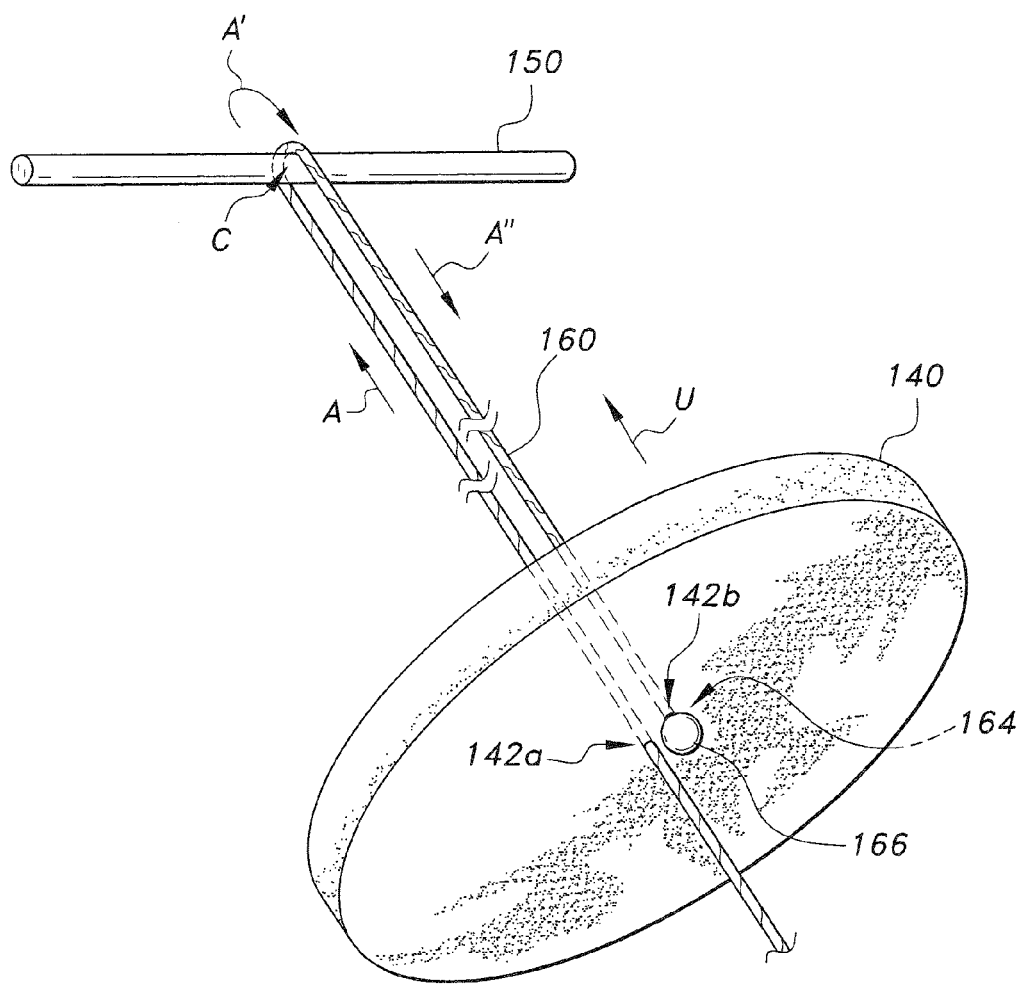
FIG. 3 is a schematic diagram of the string and disc assembly of a dispenser device according to the present invention, showing routing of the string.

The disc 140 may include a first central aperture 142*a* and a second aperture 142*b*, as shown in FIG. 3. The disc 140 has a diameter slightly less than the diameter of the tube 110, such that the disc 140 can snuggly fit within the hollow tube 110 and move upward and downward within the hollow tube 110. The disc 140 can be formed from any suitable medical grade material (preferably plastic). It is to be understood, however, that the disc 140 can also be formed from rubber or metal. If the disc 140 is formed from plastic or metal, the disc 140 can be layered or covered with a layer of rubber to improve the seal between the disc 140 and the inner surface of the hollow tube 110. Further, as referenced above, the horizontal bar 150 extends transversely across the lower end 120 of the tube 110 adjacent the lower opening 125.

Referring to FIG. 3, the string 160 can be formed from any thin, flexible, and non-elastic medical grade material. The string 160 has a first end 162 and a second end 164. The second end 164 of the string 160 is secured to the disc 140 in any suitable manner. In the embodiment shown in FIG. 3, the second end 164 extends downward threw central aperture 142a in direction A, is looped over the horizontal bar 150 at C in the direction A', extends upward in direction A" through the aperture 142b, and is secured by a knot 166. The first end 162 of the string 160 extends through the open upper end 130 of the tube 110. When the first end 162 is pulled in direction D (shown in FIG. 1), the tension placed on the disc 140 by the knot 166 pulls the disc 140 downward in the direction U, forcing any medicament P in the lower end 120 of the tube 110 out through the lower opening 125, thereby dispensing the pharmaceutical preparation P. The first end 162 of the string 160 may have a pull 168 attached thereto. The pull 168 may be a ring, ball, or other rigid object having a diameter greater than the internal diameter of the tube 110 so that the first end 162 of the string 160 does not fall back into the tube 110.

Figure 4:
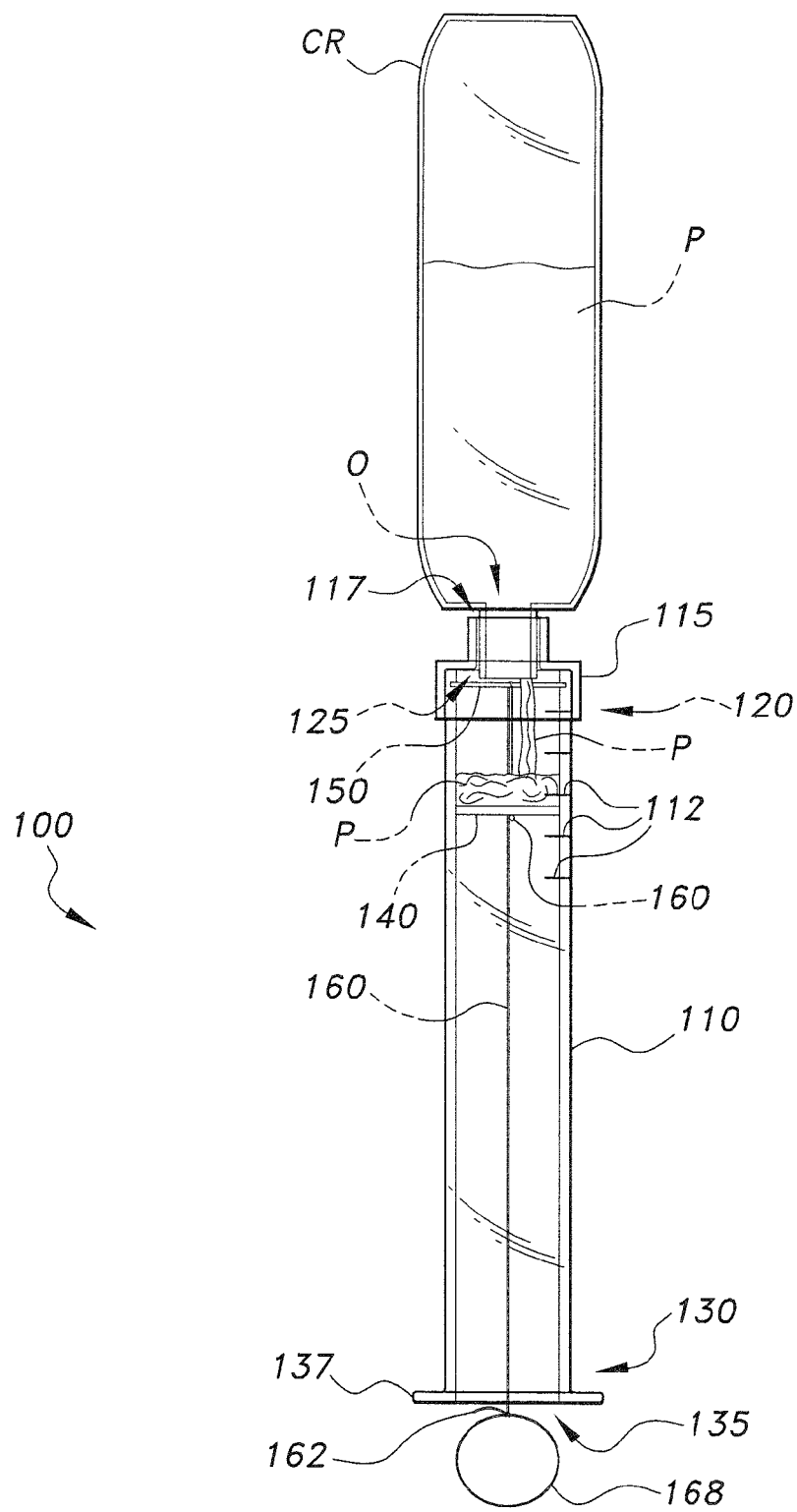
FIG. 4 is an environmental front view of a dispensing device according to the present invention, showing the device being loaded with a medicament.

As shown in FIG. 4, the device 100 is filled with the pharmaceutical preparation P through the lower opening 125 of the tube 110. Prior to filling the tube 110 with the pharmaceutical preparation P, the disc 140 is positioned at the corresponding graduation mark 112, such that the correct amount (e.g. quantity) of pharmaceutical preparation P is inserted into the device 100. If the container CR storing the pharmaceutical preparation P has an opening O that is either too big or too small to properly fit the lower opening 125 of the hollow tube 110, an adapter 115 configured for receiving the opening O of the container CR storing the pharmaceutical preparation P can be used. The adapter 115 includes an opening 117 through which the opening O of the container CR can connect with the lower opening 125 of the tube 110 to fill the device 100 with the predetermined amount of pharmaceutical preparation P. The diameter of the opening 117 of the intermediary member 115 may be adjustable to receive the opening of any container storing the pharmaceutical preparation P. The container CR may be squeezed or otherwise manipulated to press the desired volume of the pharmaceutical preparation P into the lower end 120 of the tube 110.

Alternatively, the device 100 may be pre-filled with the pharmaceutical preparation P and a cover 119 or cap (shown in FIG. 2) may be screwed or snapped onto the lower end 120 of the tube 110.

Once the device 100 is filled with the desired volume of pharmaceutical preparation P, the upper end 120 of the hollow tube 110 is inserted into the body cavity BC, e.g., the vagina or the rectum. The hollow tube 110 of the device 100 is to be inserted far enough into the body cavity BC to ensure that the pharmaceutical preparation P reaches the infected area. After the hollow tube 110 containing the pharmaceutical preparation P is inserted into the body cavity BC and has reached the desired depth, a person using the device 100 may hold the hollow tube 110 of the device 100 with index finger F1 and middle finger F2 of one hand H1, such as by grasping the flange 137, while pulling the ring 168 or other pull secured to the first end 162 of the string 160 with the index finger F3 of the other hand H2.

It is to be understood that the present invention is not limited to the embodiments described above, but encompasses any and all embodiments within the scope of the following claims.

I claim:

1. A dispensing device for dispensing a pharmaceutical preparation, comprising:
    a hollow tube, the hollow tube consisting of an outer peripheral wall, inner side walls, an open upper end, an open lower end, and an external annular flange extending around the open upper end of the tube, the open lower end defining a port, wherein the tube has a uniform internal diameter;
    a horizontal bar extending transversely between opposing inner side walls at the lower end of the tube adjacent the port;
    a disc movably disposed within the tube, the disc having a central aperture defined therein; and
    a string having a first end extending out of the open upper end of the tube and a second end secured to the disc, the string being looped around the horizontal bar and extending through the central aperture in the disc so that when the first end of the string is pulled, the disc pushes pharmaceutical preparation though the lower end of the tube to dispense the preparation.

2. The dispensing device according to claim 1, further comprising a pull attached to the first end of the string, the pull having a diameter greater than the internal diameter of the tube to keep the first end of the string outside the tube.

3. The dispensing device according to claim 1, further comprising an adapter attachable to the port, the adapter being configured for attaching a container of the pharmaceutical preparation to the port for refilling the lower end of the tube with the preparation.

4. The dispensing device according to claim 1, further comprising a cap attachable to the port for retaining the pharmaceutical preparation in the tube, wherein the cap is coextensive with the lower end of the hollow tube.

5. The dispensing device according to claim 1, wherein said tube is transparent.

6. A dispensing device for applying a semi-solid medicament to a body cavity, the device comprising:
    a hollow, transparent tube, the hollow transparent tube consisting of an outer peripheral wall, inner side walls, an open upper end and an open lower end, the open lower end defining a port, the hollow transparent tube having a uniform internal diameter, graduated indicia on the outer peripheral wall corresponding to internal volume of the tube measured from the port toward the upper end, and an external annular flange extending around the open upper end of the tube;
    a horizontal bar extending transversely between opposing inner side walls at the lower end of the tube adjacent the port;
    a disc movably disposed within the tube, the disc having a central aperture defined therein;
    a string having a first end extending out of the open upper end of the tube and a second end secured to the disc, the string being looped around the horizontal bar and extending through the central aperture in the disc so that when the first end of the string is pulled, the disc pushes pharmaceutical preparation though the lower end of the tube to dispense the preparation; and a pull attached to the first end of the string, the pull having a diameter greater than the internal diameter of the tube to keep the first end of the string outside the tube.

7. The dispensing device according to claim 6, further comprising an adapter attachable to the port, the adapter being configured for attaching a container of the pharmaceutical preparation to the port for refilling the lower end of the tube with the preparation.

8. The dispensing device according to claim 6, further comprising a cap attachable to the port for retaining the pharmaceutical preparation in the tube, wherein the cap is coextensive with the lower end of the hollow tube.

\* \* \* \* \*